United States Patent
Timmer et al.

(10) Patent No.: US 6,324,248 B1
(45) Date of Patent: Nov. 27, 2001

(54) DERIVING A CROSS-SECTIONAL DISTRIBUTION FROM AN OBJECT DATA SET

(75) Inventors: Jan Timmer; Jantje Edith Wilting, both of Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/684,194

(22) Filed: Oct. 6, 2000

(30) Foreign Application Priority Data

Oct. 7, 1999 (EP) .................................... 99203287

(51) Int. Cl.$^7$ ...................................................... A61B 6/00
(52) U.S. Cl. .................................. 378/16; 378/4; 378/20; 378/86; 378/89
(58) Field of Search ..................... 378/4, 20, 86, 378/89, 16; 528/363, 331; 428/212

(56) References Cited

U.S. PATENT DOCUMENTS

| | | | |
|---|---|---|---|
| 4,521,588 | * | 6/1985 | Rogers et al. . |
| 4,525,413 | * | 6/1985 | Rogers et al. . |
| 4,868,856 | * | 9/1989 | Frith et al. . |
| 5,847,711 | | 12/1998 | Kaufman et al. ................ 345/424 |

FOREIGN PATENT DOCUMENTS

0365141B1    4/1990    (EP) ............................... G06T/17/00

* cited by examiner

Primary Examiner—Robert H. Kim
Assistant Examiner—Pamela R. Hobden
(74) Attorney, Agent, or Firm—John Vodopia

(57) ABSTRACT

A cross-sectional distribution along a cutting plane is derived from an object data set of data values. The cross-sectional distribution comprises density values. The density values are calculated from data values of the object data set in positions outside the cutting plane. The object data set represents an object to be examined and is, for example, acquired by way of volumetric computed tomography or magnetic resonance imaging. For example, the density values of the cross-sectional distribution are calculated by local (slab) MIP or mIP or by interpolation.

9 Claims, 1 Drawing Sheet

DERIVING A CROSS-SECTIONAL DISTRIBUTION FROM AN OBJECT DATA SET

Figure 1:
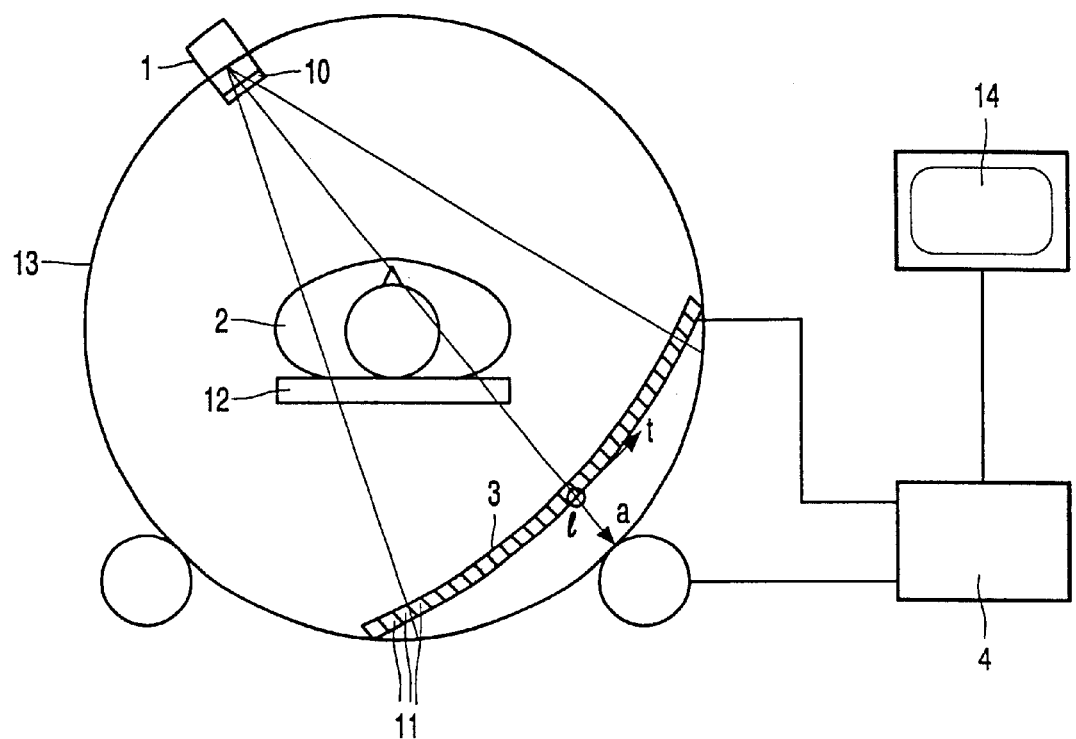

The invention relates to a method of deriving a cross-sectional distribution of density values from an object data set of data values, wherein the object data set associates data values with positions in three dimensions and represents an object, the cross-sectional distribution associates density values with positions in a cutting plane, and the cross-sectional distribution represents a cross-section along the cutting plane through the three-dimensional object.

The invention also relates to a computed tomography device.

A method and a computed tomography device of this kind are known from German Offenlegungsschrift DE 195 41 500.

The known computed tomography device includes an X-ray source and an X-ray detector which can rotate together about the object to be examined. Using the known method, the known computed tomography device acquires a plurality of cross-sectional images of the object along mutually parallel planes having a predetermined orientation. The cross-sectional images are acquired notably along a number of mutually parallel planes. This is achieved by rotating the X-ray source and the X-ray detector about the object while displacing the object and the X-ray detector and the X-ray source relative to one another. It is thus achieved that a cross-sectional image is acquired each time along the plane in which the X-ray detector and the X-ray source rotate about the object. Subsequently, the X-ray source with the X-ray detector and the object are displaced relative to one another, so that the plane in which the X-ray source and the X-ray detector rotate about the object is shifted and a next cross-sectional image is acquired. The cross-sectional images correspond to the data set and relate to a (sub-) volume of the object. An additional cross-sectional image is derived from the cross-sectional images. The additional cross-sectional image represents a cross-section through the object which has an orientation and a position within the object which can be chosen at random. The additional cross-sectional image constitutes the cross-sectional distribution. According to the known method, each time when a next cross-sectional image is acquired, the line of intersection of the plane along which the current cross-sectional image is acquired with the selected plane of the additional cross-sectional image is determined. The brightness values of the currently acquired cross-sectional image in positions on the relevant line of intersection are used as brightness values of the additional cross-sectional image. Thus, the additional cross-sectional image is composed "on-the-fly" during the acquisition of the cross-sectional images.

It is a drawback of the known method that the spatial resolution of the additional cross-sectional image differs in the directions perpendicular to and in the plane along which the cross-sectional images are acquired. Because of this direction-dependent spatial resolution, the diagnostic quality of the additional cross-sectional image is not very good.

It is an object of the invention to provide a method of deriving from the object data set a cross-sectional image which, in comparison with the result obtained by means of the known method, is a more faithful rendition of the cross-section of the object along the cutting plane.

This object is achieved by means of a method according to the invention which is characterized in that data values of the object data set in positions near and outside the cutting plane are used to calculate density values of the cross-sectional distribution.

The method according to the invention is advantageously used for forming a cross-section of a spatial object along the cutting plane from data values of the spatial object. The cross-section generally relates to a part of the interior of the object which is of importance for the examination of the object. The method utilizes an object data set of data values relating to the object. Such data values may relate to a variety of properties of the object, such as the spatial density distribution of the materials encountered in the object. Other examples in this respect are the temperature within the object, the magnetization, the electrical polarization in the object or the local elasticity of the object. The cross-section derived from the object data set by means of the method is represented by the cross-sectional distribution of density values. These density values represent the distribution along the cutting plane of the property of the object as represented by the data values.

In order to examine the interior of the object, there is determined, for example by selection, a cutting plane along which the cross-section through the object is taken. Such a cutting plane is often a flat surface through the object. It is alternatively possible to take a curved surface through the object as the cutting plane. The invention can even be suitably used for a cutting plane which extends through the object in a complex manner. The cross-sectional distribution associates density values with positions in the cutting plane. Such a position in the cutting plane usually does not coincide with a position in which a data value of the object data set is available. This is because the object data set is often constituted by data values on a three-dimensional grid. For example, a cubic grid is used. The cutting plane usually extends between the grid points of the grid of the object data set. According to the invention nearby positions with individual data values of the object data set are identified for a position in the cutting plane for which a density value is required. Notably positions outside the cutting plane are thus also identified. The density value in the relevant position in the cutting plane is calculated on the basis of the data values associated with said identified positions. Density values can thus be calculated for any desired position in the cutting plane. In a position in the cutting plane with which a data value has already been associated by the object data set, this data value can also be used to calculate the density value of the cross-sectional distribution in the relevant position. This situation occurs at the points of intersection of the cutting plane and the grid of the object data set. The density value in the relevant position in the cutting plane can be calculated from the data values of the data set in a variety of ways. A very simple calculation consists, for example, in identifying for the relevant position in the cutting plane the nearest position with a data value of the object data set and in taking this data value as the density value. Another very simple calculation is, for example, to take the data value with the maximum or minimum value of the object data set as the density value for individual positions in the cutting plane in a predetermined direction, for example perpendicular to the cutting plane and within a maximum distance from the cutting plane. This comes down to a maximum (or minimum) intensity projection (MIP and mIP, respectively) over an effective slice thickness. Accurate results are obtained for the density values of the cross-sectional distribution by, for example linear or non-linear interpolation of a plurality of data values of the object data set in positions in the vicinity of (or possibly in) the relevant positions in the cutting plane.

These and other aspects of the invention will be elaborated hereinafter on the basis of the following embodiments which are defined in the dependent Claims.

Particularly accurate results are obtained for the density values by basing the calculation of the individual density values on data values of the object data set which are associated with individual positions in the cutting plane to both sides of the cutting plane. It as been found that a faithful representation of the cross-section through the object is thus obtained.

Notably details of low contrast are thus clearly visualized in a rendition of the cross-sectional distribution. Such a rendition is, for example an image on a screen, such as a liquid crystal (LCD) display or a CRT (cathode ray tube). The brightness values of such an image represent the density values of the cross-sectional distribution. The faithful reproduction of details in the cross-sectional image according to the invention is independent of the shape of the details. Notably elongate details are faithfully reproduced; the direction in which such a detail mainly extends is irrelevant.

The calculation of the density values utilizes data values of the object data set in positions which are situated at a given distance from the cutting plane. The data values are associated with positions in a region situated within a given, predetermined maximum distance from the cutting plane. This maximum distance is preferably adjustable during the extraction of the cross-sectional distribution. This enables optimization of the contrast and the noise level in the cross-sectional distribution in dependence on the details reproduced in the cross-sectional distribution. It is alternatively possible to adjust this maximum distance prior to the extraction of the density values. Increasing the maximum distance, increases the number of data values of the object data set that will be used to calculate the density values of the cross-sectional distribution. As more data values are used, the signal-to-noise ratio of the density values of the cross-sectional distribution increases. This version is preferably used in computed tomography. The patient to be examined is then irradiated from different axial directions by means of an X-ray source emitting X-rays and density profiles are measured in the individual axial directions by means of an X-ray detector. The patient to be examined and the X-ray source with the X-ray detector are displaced relative to one another in the longitudinal direction, that is, transversely of the axial directions, in order to acquire the density profiles for a plurality of axial directions in individual longitudinal positions. The patient to be examined and the X-ray source with the X-ray detector can be alternately displaced step-wise in the longitudinal direction, density profiles then being acquired in a plurality of axial directions in successive longitudinal positions of the X-ray source and the X-ray detector relative to the patient to be examined. It is also possible to rotate the X-ray source and the X-ray detector about the patient while the X-ray source and the X-ray detector are displaced in the longitudinal direction relative to the patient to be examined. Usually the patient to be examined is displaced in the longitudinal direction while the X-ray source and the X-ray detector rotate about the patient to be examined and density profiles are acquired in a plurality of axial directions. In each of these methods of computed tomography density profiles for a three-dimensional volume of (a part of) the patient to be examined are received by the X-ray detector. The object data set is reconstructed from such density profiles, which reconstruction utilizes inter alia inverse Radon transformation. The data values of the object data set represent the local density of the patient to be examined. According to the invention the cross-sectional distribution along the cutting plane is calculated from the object data set. Because the calculation of the density values of the cross-sectional distribution utilizes data values at some distance from the cutting plane, the cross-sectional distribution corresponds to a cross-section along a slice which has a given thickness along the cutting plane. The slice thickness corresponds to the maximum distance from the cutting plane within which data values of the object data set are used to calculate density values of the cross-sectional distribution. It has been found that, notably when the object data set has been acquired by means of computed tomography, the contrast resolution increases approximately linearly as a function of the effective slice thickness. According to the invention the effective slice thickness can be controlled by adjusting the maximum distance from the cutting plane to positions whose data values of the object data set are used to calculate density values of the cross-sectional distribution. The enhancement of the signal-to-noise ratio and the contrast resolution is achieved at the expense of the spatial resolution of the cross-sectional distribution in the direction transversely of the cutting plane. The cross-sectional distribution can thus be derived in conformity with a predetermined protocol which is used notably for standard radiological examinations. As the effective slice thickness increases, the density distribution will then relate more and more to density information outside the cutting plane itself.

The invention also relates to a computed tomography device which includes an X-ray source for irradiating an object by means of X-rays from different axial directions, and an X-ray detector wherein the X-ray detector and the X-ray source and the object can be displaced relative to one another in a longitudinal direction, and the X-ray detector is arranged to measure a plurality of density profiles for respective axial directions and longitudinal positions, which density profiles form an object data set of data values, which computed tomography device includes a data processing unit for deriving a cross-sectional distribution of density values from the object data set, which cross-sectional distribution associates density values with positions in a cutting plane and represents a cross-section through the object, along a cutting plane having a given position and orientation.

It is a further object of the invention to provide a computed tomography device wherein the cross-sectional distribution can be a rendition of a cross-section of the object to be examined which is more faithful than the rendition that can be achieved by means of the known computed tomography device. This object is achieved by means of a computed tomography device according to the invention which is characterized in that the data processing unit is arranged to calculate the density values of the cross-sectional distribution from data values of the object data set in positions near the cutting plane.

Density values can thus be calculated for any desired position in the cutting plane. The computed tomography device according to the invention is preferably provided with a two-dimensional X-ray detector.

A two-dimensional X-ray detector of this kind includes a large number of, for example 1000×16 sensor elements. Such a two-dimensional X-ray detector is particularly suitable for use in a computed tomography device and is described per se in European patent application 98203651.9 (PHD 98.127). Individual sensor elements generate primary electric signals in response to incident X-rays. The signal level of the respective primary signals represents the intensity of the X-rays incident on the relevant sensor element. Subsequently, the density profiles are formed from the primary signals. The sensor elements are arranged in a two-dimensional array. For example, the X-ray detector is provided with a number of adjacently situated rows of sensor elements. The X-ray detector is mounted in the computed tomography device in such a manner that the pattern of sensor elements extends in the plane in which the X-ray source and the X-ray detector rotate about the patient to be examined, that is, in the tangential direction in said plane perpendicular to the axial directions. The two-dimensional pattern of sensor elements also extends transversely of the plane in which the X-ray source and the X-ray detector rotate about the patient, so in the longitudinal direction. Preferably, the two-dimensional pattern is designed so that the distances between the sensor elements in the longitudinal and axial directions are approximately equal. It is thus achieved that the spatial resolution is approximately the same in the longitudinal and tangential directions in the object data set formed from the density profiles. When such a two-dimensional X-ray detector is used, a plurality of density profiles can be acquired simultaneously in different longitudinal positions. Because the X-ray detector includes, for example, several rows of sensor elements in different longitudinal positions, individual rows of sensor elements can in principle acquire respective density profiles simultaneously. Thus, only a small amount of time is required to compose the object data set. The X-ray source and the X-ray detector complete a revolution about the patient to be examined in approximately 0.5 s and from 8 to 32 density profiles are acquired per second. When the density profiles are acquired by means of such a two-dimensional X-ray detector, i.e. an X-ray detector having essentially the same spatial resolution in the longitudinal and tangential directions, the spatial resolution of the object data set reconstructed therefrom is isotropic. An object data set having a substantially isotropic spatial resolution can also be formed by means of an X-ray detector whose sensor elements are arranged in a single row in the tangential direction. When use is made of such an X-ray detector comprising a single row of sensor elements, density profiles are acquired in successive longitudinal positions, the distance between neighboring longitudinal positions in which density profiles are acquired then being approximately equal to the spacing of neighboring sensor elements. The cross-sectional distribution derived from the object data set in conformity with the invention also has an isotropic spatial resolution; notably the spatial resolution of the cross-sectional distribution in the direction transversely of the longitudinal direction is substantially equal to the spatial resolution in the longitudinal direction.

Preferably, the functions of the computed tomography device according to the invention are carried out by a suitably programmed computer which is included in the computed tomography device. The computed tomography device according to the invention may also be provided with a specially designed (micro)processor with circuits for carrying out the functions of the computed tomography device according to the invention.

The invention also relates to a computer program with instructions for deriving a cross-sectional distribution of density values from an object data set of data values, wherein the object data set associates data values with positions in three dimensions and represents an object, the cross-sectional distribution associates density values with positions in a cutting plane, and the cross-sectional distribution represents a cross-section through the three-dimensional object along the cutting plane, and data values of the object data set in positions near and outside the cutting plane are used to calculate density values of the cross-sectional distribution.

Loading the computer program according to the invention into the computer of a computed tomography device, enables the method according to the invention to be carried out by means of the computed tomography device. The computer program according to the invention is stored, for example on a carrier such as a CD-ROM. The computer program is read out, for example by a CD-ROM player of the computed tomography device, so as to be stored in the memory of the computer. The computer program can alternatively be downloaded from a network, such as the world-wide web, so as to be stored in the memory of the computer.

Figure 2:
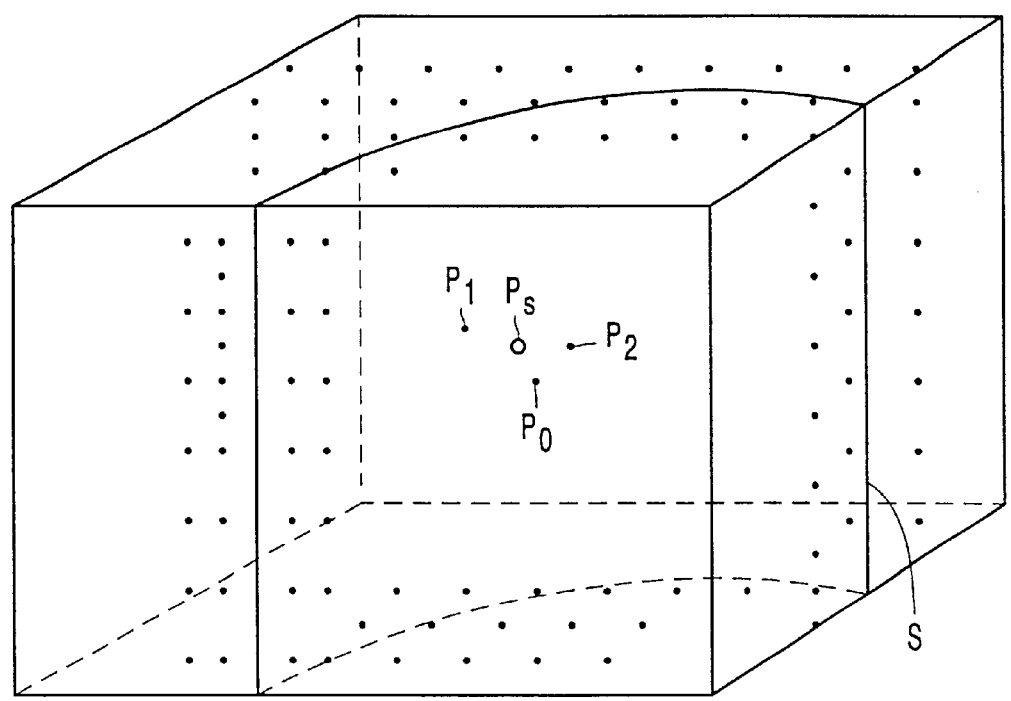

These and other aspects of the invention are apparent from and will be elucidated, by way of non-limitative example, with reference to the embodiments described hereinafter and the accompanying drawing; therein:

FIG. 1 shows diagrammatically a computed tomography device in which the invention is used, and FIG. 2 shows graphically an object data set with the cutting plane along which the density distribution is derived according to the invention.

FIG. 1 shows graphically a computed tomography device according to the invention. In cooperation with a slit-shaped collimator 10 an X-ray source 1 produces a diverging, fan-shaped or conical X-ray beam for irradiating the object 2, for example a patient to be examined. The X-ray detector 3 is arranged so as to face the X-ray source 1. The X-ray detector in the present embodiment is a position-sensitive, two-dimensional X-ray detector which includes a matrix of, for example, a plurality of parallel rows of individual detector cells 11. The detector cells 11 are, for example, gas-filled (xenon) detectors or solid-state detectors. Generally speaking, the thickness of the conical X-ray beam halfway between the X-ray source and the X-ray detector amounts to from 5 mm to 20 mm. The intensity of the radiation having traversed the patient so as to be incident on the X-ray detector is determined mainly by the absorption within the patient 2 who is positioned on a table 12 between the X-ray source and the X-ray detector. The absorption along a large number of lines is measured from a large number of axial directions by rotating the X-ray source 1 and the X-ray detector 3 together about the patient by means of a frame 13. The combined rotation of the X-ray source and the X-ray detector may be continuous but also intermittent. Furthermore, the patient can also be displaced along the axis of rotation during irradiation and rotation, that is, in the longitudinal direction, so that the X-ray detector acquires data from a significant three-dimensional volume of the patient. FIG. 1 shows the X-ray source and the X-ray detector in a cross-section through the plane in the axial direction in which the X-ray source and the X-ray detector rotate about the patient. The axial direction in the instantaneous orientation of the X-ray source and the X-ray detector is denoted by the reference (a) in the Figure. The tangential direction (t) lies in the plane in which the X-ray source 10 and the X-ray detector 3 rotate about the patient 2 and extends perpendicularly to the axial direction (a). The longitudinal direction (l) extends perpendicularly to the plane of drawing. When the X-ray source and the X-ray detector are rotated about the patient and the X-ray source with the X-ray detector and the patient on the patient table 12 are displaced in the longitudinal direction at the same time, the X-ray source and the X-ray detector describe a helical path. In that case the instantaneous plane in which the X-ray source and the X-ray detector rotate about the patient extends through the helical path in the instantaneous positions of the X-ray source and the X-ray detector and perpendicularly to the longitudinal direction. The computed tomography device may be provided not only with a rotatable system with an X-ray source and an X-ray detector, but also with a detection system which is not rotatable but extends (substantially) completely along the circumference of the patient. Generally speaking, the X-ray source and the X-ray detector together are rotated completely about the patient, so through 360°. Alternatively, a detection system can be arranged along the entire circumference of the patient, in which case the X-ray source is rotated completely about the patient. Furthermore, an X-ray source can be used in the form of an annular anode which is arranged around the patient; the target spot of an electron beam whereby X-rays are generated from the anode material then moves around the patient together with the annular anode. It is to be noted that it suffices in principle to use a fan-shaped or conical beam which rotates about the patient through an angle which equals the sum of 180° and the angle of aperture of the fan-shaped or conical beam.

Furthermore, the computed tomography device according to the invention preferably includes a two-dimensional X-ray detector. Such a two-dimensional X-ray detector includes a large number of X-ray-sensitive detector elements which are arranged in a two-dimensional pattern, for example in a plurality of rows of detector elements, said rows being adjacently situated in the longitudinal direction. When a more or less conical X-ray beam is used, density profiles can be acquired simultaneously in respective longitudinal positions. The conical beam and the two-dimensional detector notably yield an object data set with a high uniform spatial resolution, the time required for the acquisition of the density profiles not being significantly longer than in case use is made of a fan-shaped beam and an X-ray detector with a single row of detector elements.

In each position or orientation of the X-ray source and the X-ray detector the intensity of the X-rays received by the individual detector cells is digitized and applied to a reconstruction unit 4. After correction for known error sources and disturbances, the reconstruction unit 4 converts the measured data into the data values of the patient to be examined. The reconstruction unit reconstructs the data values in individual positions within the body of the patient from the density profiles for successive directions wherefrom the patient has been irradiated. The reconstruction unit 4 thus forms the object data set of data values from the density profiles measured by means of the X-ray detector. For example, high and low data values in the object data set correspond to parts of the patient in which the X-ray absorption is strong and weak, respectively. Furthermore, the reconstruction unit is arranged as a data processing unit for deriving the density distribution along the cutting plane from the object data set. The reconstruction unit includes, for example, a computer which is programmed so as to reconstruct the object data set and also to derive the cross-sectional distribution. Such a cross-sectional distribution may represent, for example a cross-section of the patient to be examined. The reconstruction unit is also arranged to form an image signal, for example, an electronic video signal, representing the cross-sectional distribution. The signal levels of such an image signal represent the density values of the cross-sectional distribution. The cross-sectional distribution can thus be displayed as an image on a monitor 14 which is coupled to the reconstruction unit. The image may also be stored as a digital image matrix or be applied to an image processing unit 15 for further processing.

FIG. 2 is a graphic representation of an object data set with the cutting plane along which the density distribution is derived according to the invention. The object data set in the example shown in FIG. 2 associates data values with positions on a three-dimensional cubic grid. FIG. 2 shows a part of the cubic grid, that is, a straight block. Positions on the three-dimensional cubic grid are called (x,y,z) and the associated values are referred to as D(x,y,z). Part of the grid points in FIG. 2 are denoted by solid spheres (•). Furthermore, FIG. 2 also shows the preselected cutting plane S as the cross-section of the cutting plane with the sides of the straight block which is shown as a part of the cubic grid. In the present example the cutting plane is a curved surface. Positions in the cutting plane are denoted by the references $(\xi,\eta,\alpha)$. In a simpler example, in which the cutting plane is a surface parallel to the (x,y) plane at $z=z_0$ of the cubic grid, it holds that $(\xi,\eta,\zeta=z_0)$. According to the invention the density value $\rho(\xi,\eta,\zeta)$ of the density distribution is derived from data values D(x,y,z) of the object data set in individual positions $(\xi,\eta,\zeta)$ in the cutting plane. For example, in the relevant position $P_s(\xi,\eta,\zeta)$ in the cutting plane the position on the cubic grid $P_0(x_0,y_0,z_0)$ is determined so that the distance between $P_s$ and $P_0$ is minimum, i.e.

$$(x_0, y_0, z_0) = \underset{x,y,z}{\operatorname{argmin}} \sqrt{(x-\xi)^2 + (y-\eta)^2 + (z-\zeta)^2}$$

and subsequently the data value in $P_0$ is taken as the density value in $P_s$, so $$\rho(\xi,\eta,\zeta)=D(x_0,y_0,z_0).$$

Interpolation of density values to both sides of the cutting plane represents another method of deriving the density value $\rho$ in $P_s$. For example, the positions $P_j(x_j,y_j,z_j)$ for j–1, . . . , N are situated to both sides of the cutting plane in the vicinity of $P_s$. In that case interpolation with weighting factors $w_j$ produces $$\rho(\xi, \eta, \zeta) = \sum_{j=1}^{N} w_j D(x_j, y_j, z_j)$$

The density values which correspond to a weighted mean value of the data values in a slice of given thickness around the cutting plane are thus calculated. N=2 in the example illustrated in FIG. 2. The density value $\rho$ is the mean value of the data values in $P_1$ and $P_2$.

The calculation of the density values can also be performed on an object data set which has been formed in advance. It is alternatively possible to calculate the density values as soon as the necessary data values in the object data set are available. For example, according to the invention it is also possible to derive the cross-section along the cutting plane "on-the-fly" during the acquisition of the density profiles.

What is claimed is:
1. A method of deriving a cross-sectional distribution of density values from an object data set of data values, wherein the object data set associates data values with positions in three dimensions and represents an object, the cross-sectional distribution associates density values with positions in a cutting plane, and the cross-sectional distribution represents a cross-section along the cutting plane through the three-dimensional object, characterized in that data values of the object data set in positions near and outside the cutting plane are used to calculate density values of the cross-sectional distribution.

2. A method as claimed in claim 1, characterized in that individual density values of the cross-sectional distribution have a value between data values in respective positions to both sides of the cutting plane.

3. A method as claimed in claim 2, characterized in that individual density values of the cross-sectional distribution are calculated by interpolation of data values in respective positions to both sides of the cutting plane.

4. A method as claimed in claim 1, characterized in that the object data set has a uniform spatial resolution along at least one longitudinal direction and one axial direction, the longitudinal and axial directions extending essentially perpendicularly to one another.

5. A method as claimed in claim 1, characterized in that the density values of the cross-sectional distribution are derived from data values of the object data set in positions situated at an adjustable maximum distance from the cutting plane.

6. A method as claimed in claim 1, wherein an X-ray source irradiates the object by means of X-rays from a plurality of axial directions, the X-ray source and the object are displaced relative to one another in a longitudinal direction, a plurality of density profiles are measured by means of an X-ray detector in a plurality of axial directions and a plurality of longitudinal positions, and wherein the object data set is formed from the density profiles.

7. A computed tomography device which includes an X-ray source for irradiating an object by means of X-rays from different axial directions, and an X-ray detector wherein the X-ray detector and the X-ray source and the object can be displaced relative to one another in a longitudinal direction, and the X-ray detector is arranged to measure a plurality of density profiles for respective axial directions and longitudinal positions, which density profiles form an object data set of data values, which computed tomography device includes a data processing unit for deriving a cross-sectional distribution of density values from the object data set, which cross-sectional distribution associates density values with positions in a cutting plane and represents a cross-section through the object along a cutting plane having a given position and orientation, characterized in that the data processing unit is arranged to calculate the density values of the cross-sectional distribution from data values of the object data set in positions near the cutting plane.

8. A computed tomography device as claimed in claim 7, characterized in that the X-ray detector is a two-dimensional detector.

9. A computer program with instructions for deriving a cross-sectional distribution of density values from an object data set of data values, wherein the object data set associates data values with positions in three dimensions and represents an object, the cross-sectional distribution associates density values with positions in a cutting plane, and the cross-sectional distribution represents a cross-section through the three-dimensional object along the cutting plane, and data values of the object data set in positions near and outside the cutting plane are used to calculate density values of the cross-sectional distribution.

\* \* \* \* \*